United States Patent
Lee et al.

(10) Patent No.: US 6,228,462 B1
(45) Date of Patent: May 8, 2001

(54) MULTILAYER COMPRESSION-RESISTANT APERTURED WEB

(75) Inventors: Yann-Per Lee, Fairfield; Hugh Joseph O'Donnell, Cincinnati, both of OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 09/079,711

(22) Filed: May 15, 1998

(51) Int. Cl.$^7$ ........................................................ B32B 3/24
(52) U.S. Cl. .......................... 428/132; 428/131; 428/137; 428/138; 428/516; 428/913; 604/378; 604/383
(58) Field of Search ..................................... 428/131, 132, 428/137, 138, 516, 913; 604/378, 383

(56) References Cited

U.S. PATENT DOCUMENTS

| | | | |
|---|---|---|---|
| 3,929,135 | 12/1975 | Thompson | 128/287 |
| 4,041,951 | 8/1977 | Sanford | 128/287 |
| 4,152,387 | 5/1979 | Cloeren | 264/171 |
| 4,197,069 | 4/1980 | Cloeren | 425/131.1 |
| 4,324,246 | 4/1982 | Mullane et al. | 128/287 |
| 4,342,314 | 8/1982 | Radel et al. | 128/287 |
| 4,395,215 | 7/1983 | Bishop | 425/290 |
| 4,463,045 | 7/1984 | Ahr et al. | 428/131 |
| 4,533,308 | 8/1985 | Cloeren | 425/131.1 |
| 4,629,643 | 12/1986 | Curro et al. | 428/131 |
| 4,637,819 | 1/1987 | Ouellette et al. | 604/369 |
| 4,747,991 | 5/1988 | Bishop | 264/504 |
| 5,006,394 | 4/1991 | Baird | 428/138 |
| 5,261,899 | 11/1993 | Visscher et al. | 604/367 |
| 5,342,334 | 8/1994 | Thompson et al. | 604/366 |
| 5,514,105 | 5/1996 | Goodman, Jr. et al. | 604/370 |
| 5,516,572 | 5/1996 | Roe | 428/131 |
| 5,520,875 | 5/1996 | Wnuk et al. | 264/504 |
| 5,733,628 | * 3/1998 | Pelkie | 428/138 |

OTHER PUBLICATIONS

"Physical Properties of Polymers Handbook", AIP Press, NY, J.E. Mark Ed., 1996, pp. 331–333.
W. Michaeli Hanser, "Extrusion Dies for Plastics and Rubber", 2$^{nd}$ Ed., NY, 1992, pp. 216–219.
U.S. application No. 08/816,106, Curro et al.
T. A. Oswald and G. Menges, "Material Science of Polymers for Engineers", Hanser Publishers, New York, NY, published in 1996 (Table 1 Guide Valves of Phys Drops of Plastics).

* cited by examiner

Primary Examiner—William P. Watkins, III
(74) Attorney, Agent, or Firm—Eileen L. Hughett; Roddy M. Bullock; Steven W. Miller

(57) ABSTRACT

An apertured, compression-resistant web is disclosed, the web comprising a first surface having a plurality of microapertures forming volcano-shaped surface aberrations, a second surface generally parallel to and spaced apart from the first surface. A plurality of fluid passageways extend between the first surface and the second surface to place the first surface and the second surface in fluid communication with one another. The web is formed of a multilayer polymeric film comprising at least one rigid layer and at least one substantially less rigid layer joined to the rigid layer. In a preferred embodiment, a rigid layer has an elastic modulus of at least 120 kpsi a substantially less rigid layer has an elastic modulus of not greater than 75 kpsi. The multilayer film is preferably formed by coextuding a rigid layer comprising a blend of polystyrene and polypropylene, and a substantially less rigid layer comprising a blend of LDPE and LLDPE.

14 Claims, 8 Drawing Sheets

MULTILAYER COMPRESSION-RESISTANT APERTURED WEB

FIELD OF THE INVENTION

The present invention relates to macroscopically expanded, three dimensional apertured polymeric webs. More particularly, the present invention relates to such webs being microapertured, and having improved compression resistance.

BACKGROUND

It has long been known in the disposable articles art that it is extremely desirable to construct absorptive devices such as disposable diapers, catamenials, sanitary napkins, incontinent articles, and the like, presenting a dry surface feel to the user. Such absorptive articles generally have a fluid pervious topsheet with a first wearer-contacting (or body-facing) surface and a second absorbent pad-contacting (or garment-facing) surface. By presenting a dry surface feel to the user, the topsheet gives improved wearing comfort, and minirnizes the development of undesirable skin conditions due to prolonged exposure to moisture absorbed within the absorptive device.

A dry surface is achieved by designing the topsheet to have both fluid transport and fluid retaining characteristics. Desirable fluid transport characteristics allow the topsheet to acquire fluids, such as urine or menses, and pass the fluid into the absorptive article. Once absorbed into the absorptive article, the fluid retaining feature of the topsheet preferably prevents rewet, i.e., the movement of fluid back through the topsheet. Rewet can be a result of at least two causes: (1) squeezing out of the absorbed fluid due to pressure on the absorptive article; and/or (2) wetness entrapped within or on the topsheet. Preferably, both properties, fluid acquisition and fluid retention, are maximized. Said differently, preferably a topsheet will exhibit high rates of fluid acquisition, and low levels of rewet.

While woven and nonwoven fibrous webs are often employed as topsheets on disposable absorbent garments because of their pleasant surface feel, polymeric formed film webs have been shown to exhibit more desirable fluid transport and fluid retention characteristics in many circumstances. For example, one viable prior art solution is disclosed in commonly assigned U.S. Pat. No. 4,342,314 issued to Radel et al. on Aug. 3, 1982 and hereby incorporated herein by reference. Radel et al. discloses an absorbent article with a wearer-contacting topsheet comprising a resilient macroscopically expanded, three-dimensional, plastic web exhibiting a combination of fiber-like and plastic properties. The web's fiber-like appearance is due to a continuum of fiber-like elements, wherein the opposed ends of each of the fiber-like elements are interconnected to at least one other of the fiber-like elements.

A topsheet of the type generally disclosed by Radel et al. is highly effective in promoting rapid fluid transfer from the wearer-contacting surface to the second absorbent pad-contacting surface of the topsheet. Accordingly, topsheets of this type have enjoyed widespread commercial success on catamenial pads due to their clean and dry appearance in use when contrasted to conventional nonwoven fibrous topsheets. While the Radel et al. topsheet is highly effective in promoting rapid transfer of bodily fluids from the first wear-contacting surface to the second absorbent pad-contacting surface, there remains some negative consumer reaction to placing polymeric webs comprised of plastic in contact with the user's skin.

Because of the superior fluid handling characteristics that can be provided in polymeric webs of the aforementioned type and their inherent cost advantages when contrasted to woven and non-woven fibrous webs, considerable effort has been expended to improve the consumer's reaction to the use of polymeric webs in contact with the skin. For example, an improved macroscopically expanded three-dimensional polymeric web exhibiting a substantially non-glossy visible surface and cloth-like tactile impression is disclosed in commonly assigned U.S. Pat. No. 4,463,045 issued to Ahr et al. on Jul. 31, 1984. The visible surface of the macroscopically expanded three-dimensional polymeric web of Ahr et al. is preferably provided with a regularly spaced, microscopic pattern of surface aberrations, the pattern being too fine to be discernible by the normal naked eye when the perpendicular distance between the viewer's eye and the plane of the web is about 12 inches. The pattern, however, is highly effective in substantially eliminating specular reflection of incident light.

U.S. Pat. No. 4,629,643, issued to Curro et al. on Dec. 16, 1986 discloses a particularly effective solution to providing a polymeric web exhibiting a soft and silky tactile impression. Curro et al. discloses a microapertured polymeric web having a fine scale pattern of discrete surface aberrations. Unlike prior art webs such as those disclosed in the aforementioned patent to Ahr et al., at least one tiny aperture, i.e., a microaperture, is provided substantially coincidental with the maximum amplitude of each surface aberration. The discontinuity created by the aperture at the peak of each surface aberration substantially reduces its resistance to compression and shear and significantly alters the tactile response of the web. The microapertured web of Curro et al. not only appears substantially non-glossy, but, in addition, exhibits a soft and silky tactile impression which appears to be preferred by many consumers. The aforementioned Curro '643 patent is hereby incorporated herein by reference.

While the Curro '643 microapertured web exhibits superior softness and tactile impression, as well as superior fluid acquisition rates, experience has shown that topsheets made with such webs can have relatively poor rewet properties as compared to other formed-film apertured webs, such as those disclosed generally in the aforementioned Radel patent. Without being bound by theory, it appears the limited compression resistance of the Curro '643 web tends to make it more susceptible to rewet under pressure. Because rewet properties contribute to overall dryness and cleanliness to the consumer, this drawback could limit consumer acceptance of apertured or microapertured webs.

Accordingly, it would be desirable to provide a soft, porous web having improved compression resistance.

Additionally, it would be desirable to provide a soft, porous web having superior fluid transport and fluid restraining characteristics.

Further, it would be desirable to provide an absorbent article having a soft, porous topsheet having superior improved resistance to compression under pressure.

SUMMARY OF THE INVENTION

An apertured, compression-resistant web is disclosed, the web comprising a first surface having a plurality of microapertures forming volcano-shaped surface aberrations, a second surface generally parallel to and spaced apart from the first surface. A plurality of fluid passageways extend between the first surface and the second surface to place the first surface and the second surface in fluid communication with one another. The web is formed of a multilayer polymeric film comprising at least one rigid layer and at least one substantially less rigid layer joined to the rigid layer.

In a preferred embodiment, a rigid layer has an elastic modulus of at least 120 kpsi, and a substantially less rigid layer has an elastic modulus of not greater than 75 kpsi. The multilayer film is preferably formed by coextuding a rigid layer comprising a blend of polystyrene and polypropylene, and a substantially less rigid layer comprising a blend of LDPE and LLDPE.

BRIEF DESCRIPTION OF THE DRAWINGS

While the specification concludes with claims particularly pointing out and distinctly claiming the subject matter of the present invention, it is believed that the present invention will be better understood from the following description taken in conjunction with the accompanying drawings in which like reference numerals identify identical elements and wherein:

FIGS. 9 A,B–C are cross sectional representations of a web of the present invention at three different points of the microaperturing and macroaperturing process.

DETAILED DESCRIPTION OF THE PRESENT INVENTION

Figure 1:
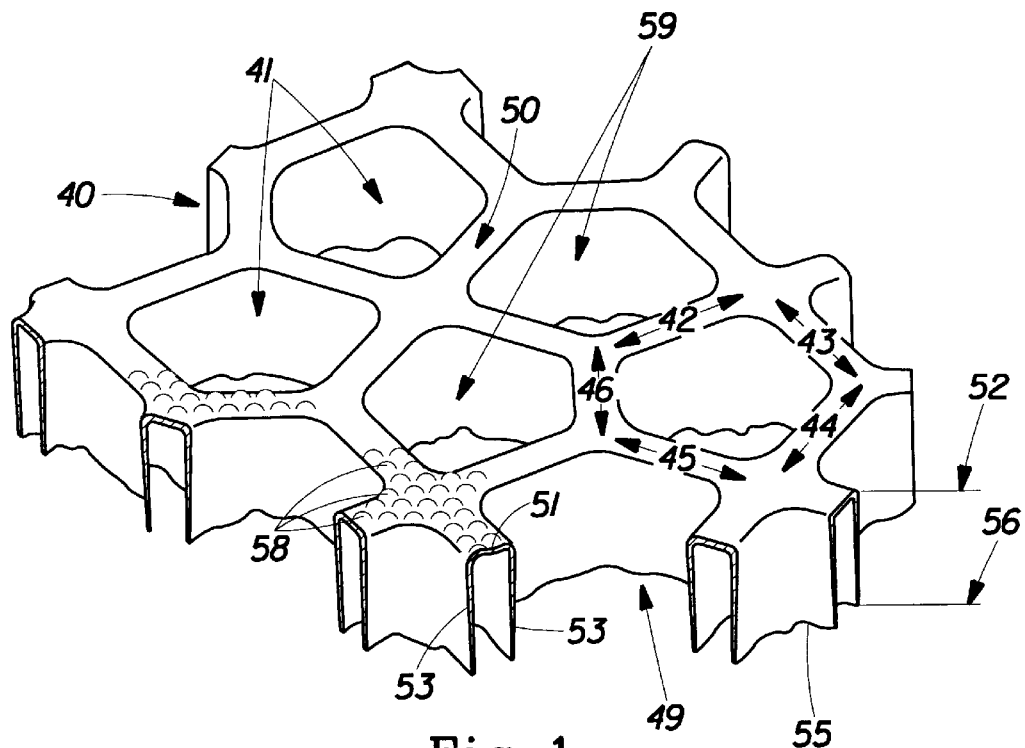
FIG. 1 is an enlarged, partially segmented, perspective illustration of a prior art polymeric web of a type generally disclosed in commonly assigned U.S. Pat. No. 4,342,314.

FIG. 1 is an enlarged, partially segmented, perspective illustration of a prior art macroscopically-expanded, three-dimensional, fiber-like, fluid pervious polymeric web 40 which has been found highly suitable for use as a topsheet in disposable absorbent articles, such as diapers and sanitary napkins. The prior art web is generally in accordance with the teachings of commonly assigned U.S. Pat. No. 4,342,314 issued to Radel et al. on Aug. 3, 1982, which is hereby incorporated herein by reference. The fluid pervious web 40 exhibits a multiplicity of apertures, e.g., apertures 41, which are formed by a multiplicity of interconnected fiber-like elements, e.g., fiber-like elements 42, 43, 44, 45, and 46 interconnected to one another in the first surface 50 of the web. Each fiber-like element comprises a base portion, e.g., base portion 51, located in plane 52 of the first surface 50. Each base portion has a sidewall portion, e.g., sidewall portion 53, attached to each edge thereof. The sidewall portions extend generally in the direction of the second surface 55 of the web. The intersecting sidewall portions of the fiber-like elements are interconnected to one another intermediate the first and second surfaces of the web, and terminate substantially concurrently with one another in the plane 56 of the second surface 55.

In a preferred embodiment, the base portion 51 includes a microscopic pattern of surface aberrations 58, which can be generally in accordance with the teachings of U.S. Pat. No. 4,463,045, issued to Ahr et al. on Jul. 31, 1984, the disclosure of which is hereby incorporated herein by reference. When present according to the teachings of Ahr et al., the microscopic pattern of surface aberrations 58 provides a substantially non-glossy visible surface when the web 40 is struck by incident light rays. In a more preferred embodiment, surface aberrations 58 can be hydroformed microapertures in accordance with the teachings of U.S. Pat. No. 4,629,643, issued to Curro et al. on Dec. 16, 1986, the disclosure of which is hereby incorporated herein by reference.

In an alternative embodiment the prior web may include a multiplicity of much smaller capillary networks (not shown) in the first surface 50 of the web, as taught by U.S. Pat. No. 4,637,819 to Ouellette et al. issued Jan. 20, 1987 and hereby incorporated herein by reference. It is believed that the additional porosity afforded by the smaller fluid-handling capillary networks may allow the web 40 function more efficiently when used as an extensible, porous portion of a disposable absorbent article.

As utilized herein, the term "interconnecting members" refers to some or all of the elements of the web 40, portions of which serve to define the primary apertures by a continuous network. Representative interconnecting members include, but are not limited to, the fiber-like elements of the aforementioned '314 Radel et al. patent and commonly assigned U.S. Pat. No. 5,514,105 to Goodman, Jr., et al. issued on May 7, 1996 and hereby incorporated herein by reference. As can be appreciated from the following description and drawings, the interconnecting elements are inherently continuous, with contiguous interconnecting elements blending into one another in mutually-adjoining transition portions.

Individual interconnecting members can best be described, with reference to FIG. 1, as those portions of web 40 disposed between any two adjacent primary apertures, originating in the first surface 50 and extending to the second surface 55. On the first surface of the web the interconnecting members collectively form a continuous network, or pattern, the continuous network of interconnecting members defining the primary apertures, and on the second surface of the web the interconnecting sidewalls of the interconnecting members collectively form a discontinuous pattern of secondary apertures. Interconnecting members are further generally described below with reference to FIG. 6.

As utilized herein, the term "continuous", when used to describe the first surface of the web, refers to the uninterrupted character of the first surface, generally in the plane of the first surface. Thus, any point on the first surface can be reached from any and every other point on the first surface without substantially leaving the first surface in the plane of the first surface. Likewise, as utilized herein, the term "discontinuous," when used to describe the second surface of the web, refers to the interrupted character of the second surface, generally in the plane of the second surface. Thus, any point on the second surface cannot be reached from every other point on the second surface without substantially leaving the second surface in the plane of the second surface.

In general, as utilized herein the term "macroscopic" is used to refer to structural features or elements which are readily visible to a normal human eye when the perpendicular distance between the viewer's eye and the plane of the web is about 12 inches. Conversely, the term "microscopic" is utilized to refer to structural features or elements which are not readily visible to a normal human eye when the perpendicular distance between the viewer's eye and the plane of the web is about 12 inches.

As utilized herein, the term "macroscopically-expanded", when used to describe three-dimensional webs, ribbons and films, refers to webs, ribbons and films which have been caused to conform to the surface of a three-dimensional forming structure so that both surfaces thereof exhibit the three-dimensional pattern of the forming structure. Such macroscopically-expanded webs, ribbons and films are typically caused to conform to the surface of the forming structures by embossing (i.e., when the forming structure exhibits a pattern comprised primarily of male projections), by debossing (i.e., when the forming structure exhibits a pattern comprised primarily of female capillary networks), or by extrusion of a resinous melt onto the surface of a forming structure of either type.

By way of contrast, the term "planar" when utilized herein to describe plastic webs, ribbons and films, refers to the overall general condition of the web, ribbon or film when viewed by the naked eye on a macroscopic scale. For example, a non-apertured extruded film or an apertured extruded film that does not exhibit significant macroscopic deformation out of the plane of the film would generally be described as planar.

When macroscopically-expanded, the interconnecting members may be described as channel-like. Their two-dimensional cross-section may also be described as "U-shaped", as in the aforementioned Radel et al. patent, or more generally as "upwardly concave-shaped", as disclosed in the aforementioned Goodman, Jr., et al. patent. "Upwardly concave-shaped" as used herein describes the orientation of the channel-like shape with relation to the surfaces of the web, with the base generally in the first surface, and the legs of the channel extending from the base in the direction of the second surface, and with the channel opening being substantially in the second surface. In general, for a plane extending through the web orthogonal to the plane of the first surface and intersecting any two adjacent primary apertures, the resulting cross-section of an interconnecting member disposed between will exhibit a generally upwardly concave shape that may be substantially U-shaped.

Figure 2:
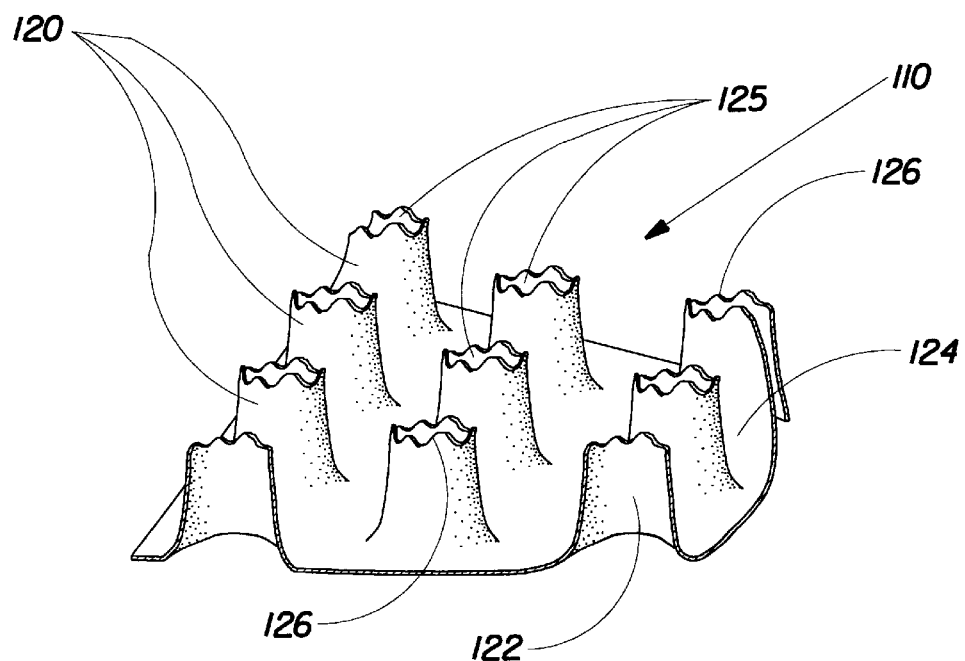
FIG. 2 is an enlarged, partially segmented, perspective illustration of a prior art polymeric web of a type generally disclosed in commonly assigned U.S. Pat. No. 4,629,643.

FIG. 2 is an enlarged, partially segmented, perspective illustration of a segment of a prior art microapertured polymeric web 110, preferably formed generally in accordance with the teachings the aforementioned Curro '643 patent. The microapertures are formed on the film prior to macroscopically expanding the film to form a substantially uniform distribution of surface aberrations on the macroscopically expanded web. Microapertures 125 can be formed by a hydroformation process in which a high pressure liquid jet is preferably utilized to force the web to conform to a woven wire support member. Because of the greater driving force applied by the liquid jet, those portions of the web which coincide with the interstices formed by the intersecting filaments in the woven wire support member are ruptured to form tiny apertures, i.e., microapertures 125 at points which coincide substantially with the maximum amplitude of each surface aberration 120. As can be seen in FIG. 2, rupturing of the surface aberrations 120 at these points results in the formation of a volcano-shaped aperture 125 having relatively thin, irregularly shaped petals 126 about its periphery. A detailed method of forming is disclosed below with reference to FIG. 9.

One drawback associated with prior art macroscopically-expanded, three-dimensional webs, as shown in FIG. 1, is that some consumers objected to placing polymeric webs comprised of plastic in contact with their skin. Microaperturing the macroscopically-expanded web, such as with microapertures shown as the surface aberrations in FIG. 2, gives the web improved softness and tactile impression, thereby making the web more clothlike, and less plastic-like.

Even though a microapertured, macroscopically-expanded web provides greatly enhanced softness, it has been found that it is more susceptible to collapse under pressure. This collapse under pressure causes the web to be less efficient at preventing rewet during use. Without being bound by theory, it appears that the increased susceptibility to collapse under pressure is due to the decreased compression resistance of the microapertured web. Due to the plurality of microaperture openings, which include openings in the sidewalls of the interconnecting members, microapertured webs may not have the structural rigidity to withstand normal use pressure, and retain or recover a certain standoff, i.e., a certain distance between the first surface and the second surface of the web.

Therefore, without being bound by theory, it appears that the increased susceptibility to rewet under pressure for microapertured, macroscopically-expanded webs is due to the decreased compression resistance of the microapertured web. As the caliper of the microapertured, macroscopically-expanded web decreases with increasing use pressure, the amount of rewet also increases. Testing has shown that one of the most important design factors contributing to improved rewet properties in three-dimensional formed films is topsheet "stand-off". Topsheet stand-off generally refers to the vertical (i.e., Z-direction) distance, or spacing, between the first body-facing surface of the web, and the second, garment facing surface of the web. More specifically, topsheet standoff refers to the distance between the skin (or hairs) of the wearer and the absorbent core of an absorbent article.

It has been discovered that if a relatively rigid film can be formed into a microapertured, macroscopically-expanded, three-dimensional, fluid pervious web, generally in accordance with the teachings of the aforementioned Curro '643 patent, the resulting microapertured web exhibits the desirable rewet properties of non-microapertured webs, e.g., macroscopically-expanded webs generally of the aforementioned Radel et al. patent. The improved rewet properties are believed to be due to the improved compression resistance of the web. However, the desirable rewet properties are gained at the expense of softness, because the rigid film increases the stiffness of the entire web, including the volcano-shaped apertures.

Figure 3:
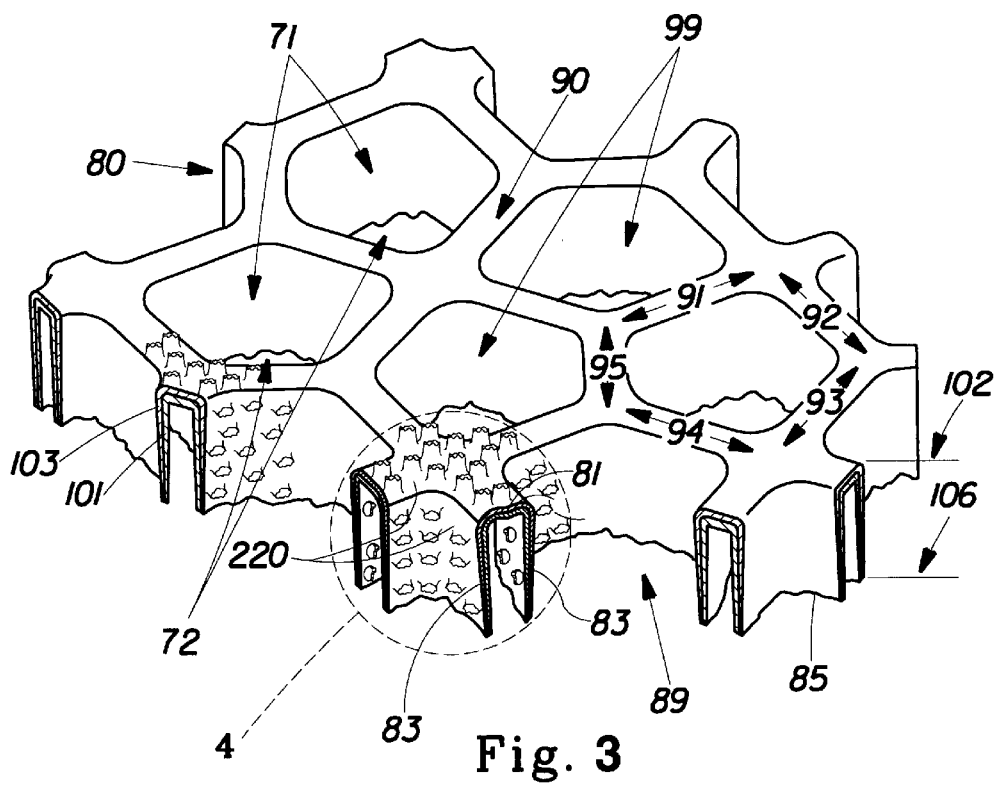
FIG. 3 is an enlarged, partially segmented, perspective illustration of a preferred compression resistant web of the present invention having two layers of polymer film, at least one of which is a rigid layer, and at least one of which is a substantially less rigid layer.

The problems associated with providing a soft, clothlike, compression-resistant webs for use as topsheets in absorbent articles are overcome with a web of the present invention, shown in FIG. 3. By utilizing a multilayer polymeric film comprising at least one rigid layer, and at least one substantially less rigid layer, and forming the multilayer web into a microapertured, macroscopically-expanded, three-dimensional configuration, the technical contradiction between softness and compression resistance is resolved. Likewise, when used as a topsheet on an absorbent article, the web of the present invention offers softness while exhibiting superior fluid transport properties, including fluid acquisition, and reduced rewet, as compared to prior art microapertured, macroscopically-expanded webs.

As used herein, "rigid" materials include any material having an elastic modulus of at least 120 kpsi. As used herein, "substantially less rigid" materials include materials having an elastic modulus of not greater than 75 kpsi. Elastic moduli of materials may be determined by reference to data in published materials such as "Material Science of Polymers for Engineers" by T. A. Oswald and G. Menges, published in 1996 by Hanser Publishers, New York, N.Y. Elastic moduli may also be determined directly by testing, such as by the method set forth in ASTM D638.

Web Embodiment

FIG. 3 shows an enlarged partially segmented, perspective illustration of a microapertured, macroscopically-expanded, three-dimensional, compression resistant web embodiment of the present invention, generally indicated as 80. The geometrical configuration of the fluid-pervious, compression resistant web 80 is generally similar to that of prior art web 40, illustrated in FIG. 1, and is generally in accordance with the teachings of the aforementioned '314 Radel et al. and "643 Curro et al. patents. Other suitable formed film patterns and configurations are described in commonly-assigned, copending, U.S. patent application Ser. No. 08/816,106, filed Mar. 14, 1997; U.S. Pat. No. 3,929,135, issued to Thompson on Dec. 30, 1975; U.S. Pat. No. 4,324,246 issued to Mullane, et al. on Apr. 13, 1982; and U.S. Pat. No. 5,006,394 issued to Baird on Apr. 9, 1991. The disclosures of each of these applications and patents are hereby incorporated herein by reference.

A preferred embodiment of a compression resistant web 80 of the present invention exhibits a multiplicity of primary apertures, e.g., primary apertures 71, which are formed in plane 102 of the first surface 90 by a continuous network of interconnecting members, e.g., members 91, 92, 93, 94, 95 interconnected to one another. Primary apertures are also termed "apertures" or "macroapertures" herein, as opposed to "microapertures" present as "volcano-shaped" surface aberrations 220 on a web of the present invention. Macroapertures are the result of macroscopically-expanding a planar web; in general the planar web may or may not be microapertured.

The shape of primary apertures 71 as projected on the plane of the first surface 90 may be in the shape of polygons, e.g., squares, hexagons, etc., in an ordered or random pattern. In a preferred embodiment primary apertures 71 are in the shape of modified ovals, in a staggered pattern, as described below with reference to FIG. 10.

In a preferred embodiment each interconnecting member comprises a base portion, e.g., base portion 81, located in plane 102, and each base portion has a sidewall portion, e.g., sidewall portions 83, attached to each edge thereof. The sidewall portions 83 extend generally in the direction of the second surface 85 of the web and intersect with side walls of adjoining interconnecting members. The intersecting sidewall portions are interconnected to one another intermediate the first and second surfaces of the web, and terminate substantially concurrently with one another to form a secondary aperture, e.g., secondary apertures 72 in the plane 106 of the second surface 85.

Figure 4:
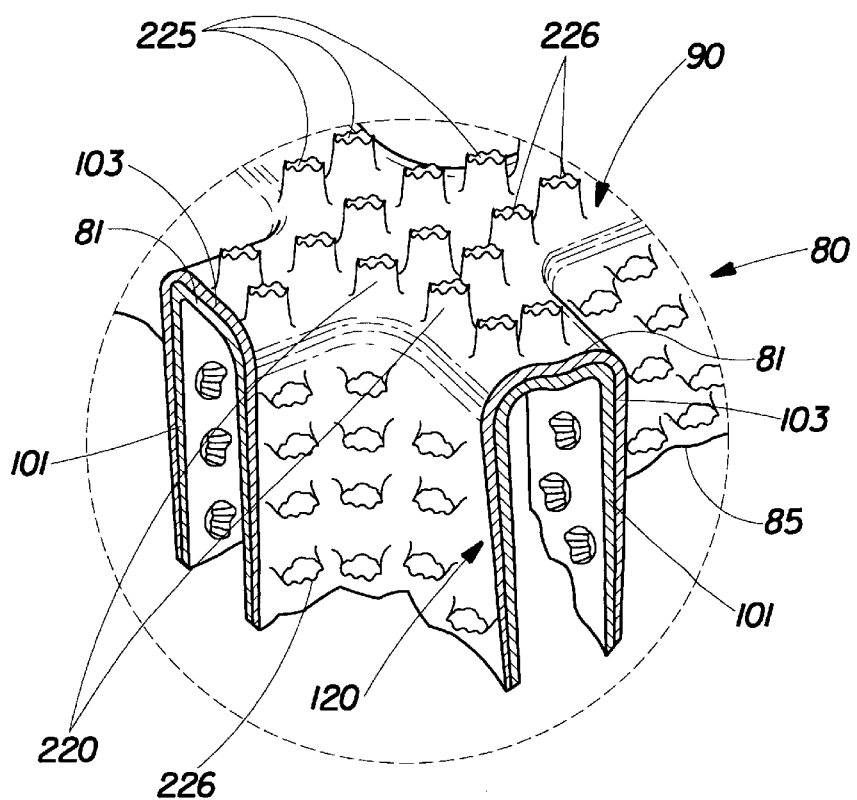
FIG. 4 is a further enlarged, partial view of a web of the type generally shown in FIG. 3, but illustrating in greater detail the web construction of a compression resistant web of the present invention.

FIG. 4 is a further enlarged, partial view of a web 80 shown in FIG. 3. The multilayer polymeric formed film 120 of web 80 is preferably comprised of at least one rigid layer 103, and at least one substantially less rigid layer 101. While FIGS. 3 and 4 show a two-layer embodiment with the rigid layer 103 nearer the first surface 90, it is believed that the order of layering of the formed film 120 shown is not limiting. While it is presently preferred that, as shown in FIG. 4, the polymeric layers terminate substantially concurrently in the plane of the second surface, it is not presently believed to be essential that they do so, i.e., one or more layers may extend further toward the second surface than the others. Microapertures 225 are formed on the film prior to macroscopically expanding the film to form a substantially uniform distribution of surface aberrations 220 on the macroscopically expanded web. Microapertures 225 can be formed by a hydroformation process at points which coincide substantially with the maximum amplitude of each surface aberration 220. As can be seen in FIG. 2, rupturing of the surface aberrations 220 at these points results in the formation of a volcano-shaped aperture 225 having relatively thin, irregularly shaped petals 226 about its periphery.

Figure 5:
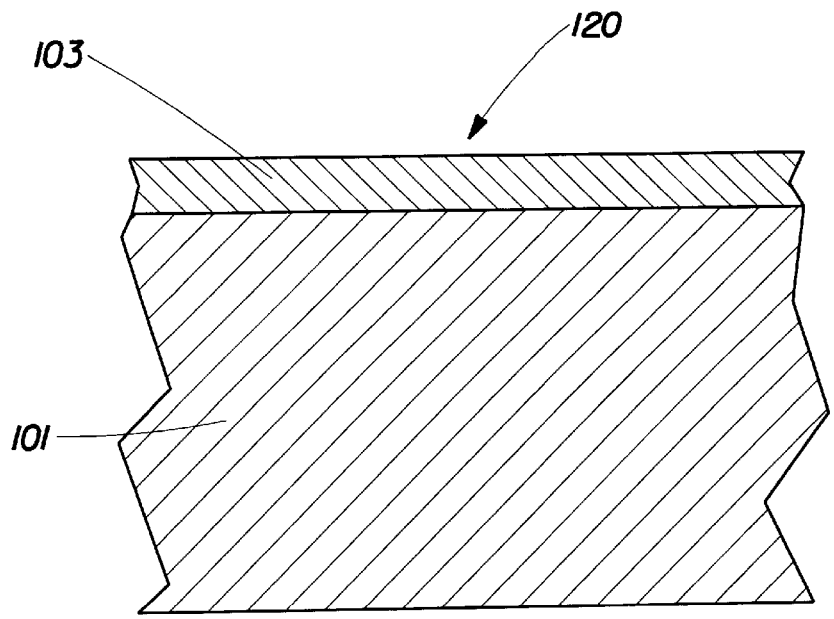
FIG. 5 is a partially segmented cross-sectional illustration of a two-layer embodiment of a film of the compression resistant web of the present invention.

A particularly preferred multilayer polymeric film 120 capable of being formed into a web 80 of the present invention is depicted in cross-section in FIG. 5. As shown in FIG. 4, rigid layer 103 can be coextruded together with a substantially less rigid layer 101. In a preferred embodiment, the thickness (caliper) of rigid layer 103 is from about 5% up to about 40% the total film thickness. In a more preferred embodiment, the thickness of the rigid layer 103 is from about 5% to about 20% of the total film thickness. In a most preferred embodiment, the thickness of the rigid layer is approximately 10% or less of the total film thickness, and may be termed a "skin layer".

The film configuration depicted in FIG. 5 represents a currently preferred arrangement, but other layering configurations are contemplated. For example, it may be beneficial to have a rigid skin layer on both sides of a substantially less rigid layer in a three-layer laminate to provide added compression resistance. Conversely, having a rigid skin layer "sandwiched" between two substantially less rigid layers may provide extra softness. Various other combinations of multiple layer designs may enhance softness, compression resistance, or both in varying proportions.

The rigid layer comprises material having an elastic modulus of greater than about 120 kpsi, and can be formed with the less rigid layer into a web of the present invention, as depicted in cross-section in FIG. 5. Some materials exhibiting suitable moduli that are greater than about 120 psi can be found in handbooks such as *Physical Properties of Polymers Handbook*, AIP Press, New York, J. E. Mark Ed., 1996 which is hereby incorporated herein by reference.

In one embodiment, the rigid layer 103 can comprise polypropylene having an elastic modulus of from about 155 kpsi, up to about 290 kpsi. In another embodiment the rigid layer can comprise polystyrene (having an elastic modulus from about 350 kpsi, up to about to 460 kpsi), particularly if blended with other thermoplastic materials. In one embodiment, the rigid layer 103 is a 70/30 blend of polypropylene/polystyrene (i.e., 70% polypropylene, 30% polystyrene), having a modulus intermediate to that of either polypropylene and polystyrene. Other materials suitable for use as the rigid layer include high density polyethylene, nylon, polycarbonate, poly(methyl methacrylate), poly(ethylene terephthalate) (or polyesters) and its copolymers such as poly(ethylene 1,4-cyclohexylenedimethylene terepthalate) as sold by Eastman Chemical Company, and other copolymers such as poly(acrylonitrile-butadiene-styrene), and poly(styrene-acrylonitrile) as sold by Dow Chemical Company, and poly(propylene-styrene) and poly(propylene-methyl methacrylate) as sold by Montell Polyolefins under the Hivalloy® tradename , or blends of these materials. Additives commonly used in the art, such as fillers, pigments, lubricating aids, and antioxidants, may also be included in the film structure.

The substantially less rigid layer 101 comprises a material having an elastic modulus not greater than about 75 kpsi. Suitable materials for the substantially less rigid layer include polyethylene (including low density polyethylene and linear low density polyethylene) having elastic moduli as low as about 28 kpsi, and ethylene vinyl acetate (EVA), having an elastic moduli less than about 25 kpsi and generally greater than 3 kpsi. Other materials suitable for use as the substantially less rigid layer 101 include metallocene polyethylene with densities between about 0.90 and 0.93 g/cc, ethylene acrylate copolymers such as methyl acrylate, and ethylene propylene copolymers such as Adflex® sold by Montell Polyolefins in Wilmington, Del. Blends of low modulus materials may also be used. For example, the substantially less rigid layer can comprise a 50/50 blend of low density polyethylene and linear low density polyethylene (i.e., 50% LDPE, 50% LLDPE). Soft rubbery materials may also be used in the substantially less rigid layer. These rubbery materials include styrenics such as styrene butadiene styrene and styrene ethylene butylene styrene copolymers. Other rubbery materials include ethylene propylene rubbers or ethylene propylene diene rubbers such as typically used in manufacture of thermoplastic elastomers.

A preferred method to produce the multilayer polymeric film 120 is coextrusion, as discussed in detail below. To be coextruded, the rigid layer should have sufficient adhesion to the substantially less rigid layer such that it will not delaminate either before, during, or after further processing. Dissimilar materials such as polystyrene and polyethylene, when coextruded, may not exhibit good adhesion to one another, so an adhesive layer may be needed to provide adequate adhesion for sufficient film integrity. By "adequate adhesion" is meant that the two (or more) layers are joined sufficiently so as to not delaminate during further processing. The layers may be joined substantially continuously over the entire layer, or they may be bonded at discrete, discontinuous areas such as a uniform pattern of closely-spaced spot bonds.

To circumvent the need for an adhesive layer, some thermoplastic materials, even dissimilar materials, may be blended and used in the rigid layer, provided that at least one of the materials exhibits adequate adhesion to the substantially less rigid layer, and it is present in sufficient quantity at the material interface to provide adequate adhesion. The primary advantage to blending materials in the rigid layer is that the modulus can be increased by blending higher modulus, but non-adhering, components with lower modulus, but adhering, components. By using a greater quantity of adhering components adequate film integrity can be obtained.

Figure 6:
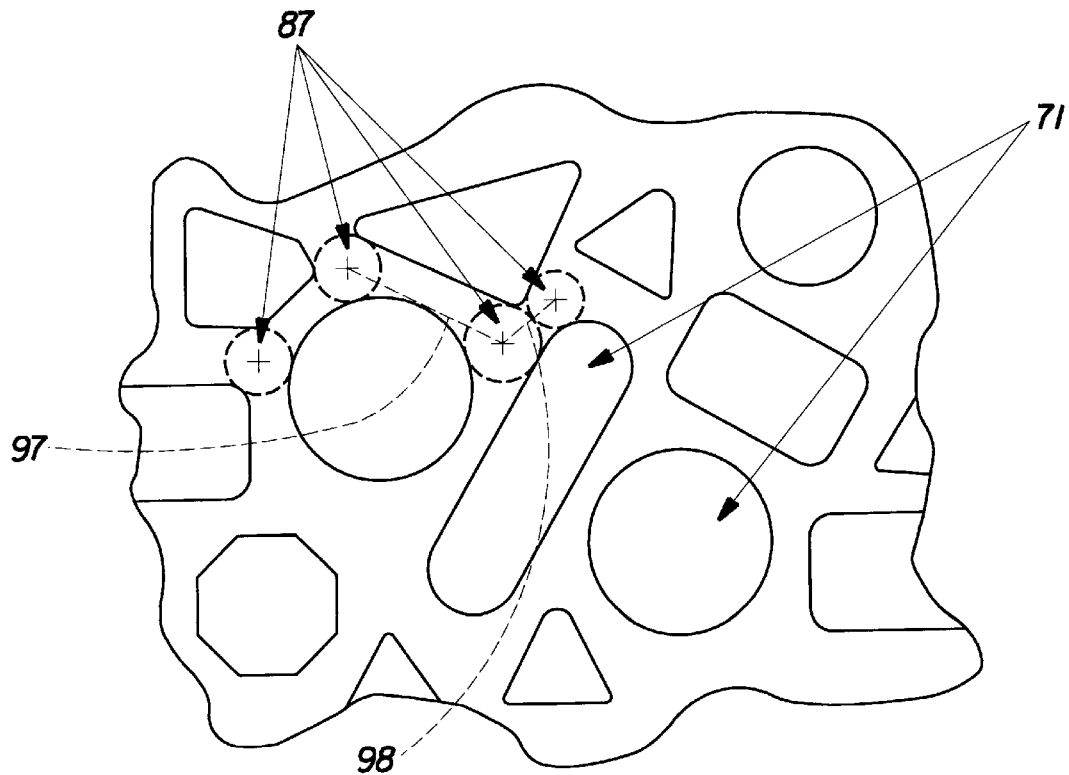
FIG. 6 is a plan view of representative aperture shapes projected in the plane of the first surface of an alternative compression resistant web of the present invention.

FIG. 6 is a plan view of alternative primary aperture shapes projected in the plane of the first surface of an alternative compression resistant web of the present invention. While a repeating pattern of uniform shapes is preferred, the shape of primary apertures, e.g., apertures 71, may be generally circular, polygonal, or mixed, and may be arrayed in an ordered pattern or in a random pattern. Although not shown, it is understood that the projected shape may also be elliptical, tear-drop shaped, or virtually any other shape, that is, the present invention is believed to be aperture-shape independent.

As shown in FIG. 6, the interconnecting elements are inherently continuous, with contiguous interconnecting elements blending into one another in mutually-adjoining transition zones or portions, e.g., transition portions 87. In general, transition portions are defined by the largest circle that can be inscribed tangent to any three adjacent apertures. It is understood that for certain patterns of apertures the inscribed circle of the transition portions may be tangent to more than three adjacent apertures. For illustrative purposes, interconnecting members may be thought of as beginning or ending substantially at the centers of the transition portions, such as interconnecting members 97 and 98. Likewise, the sidewalls of the interconnecting members can be described as interconnecting to sidewalls of contiguous interconnecting members.

Exclusive of portions of the transition zones, cross-sections transverse to a center line between the beginning and end of interconnecting members are preferably of generally uniform U-shape. However, the transverse cross-section need not be uniform along the entire length of the interconnecting member, and for certain aperture configurations it will not be uniform along most of its length. In particular, in transition zones or portions 87, interconnecting members blend into contiguous interconnecting members and transverse cross-sections in the transition zones or portions may exhibit substantially non-uniform U-shapes, or no discernible U-shape. Further discussion of cross section structure is disclosed in the aforementioned U.S. patent application Ser. No. 08/816,106.

Absorbent Article

Figure 7:
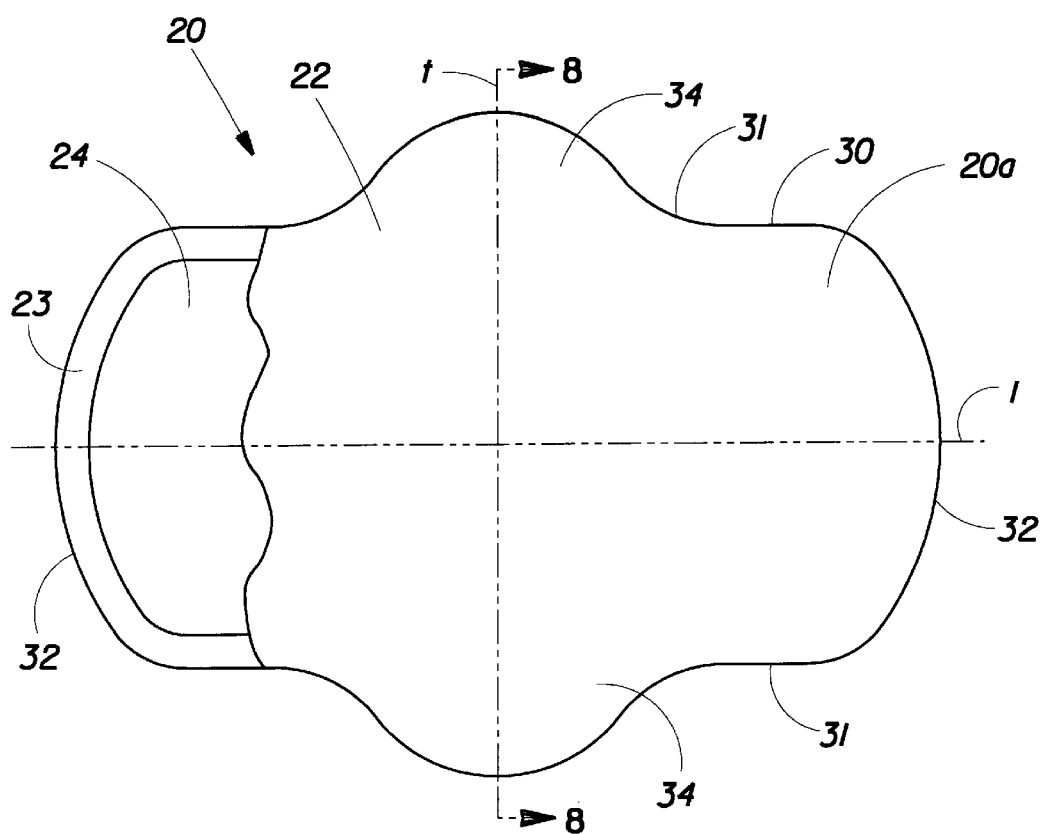
FIG. 7 is a top plan view of a sanitary napkin with portions cut way to more clearly show the construction of the sanitary napkin.

A representative embodiment of a compression resistant web of the present invention utilized as a topsheet in a disposable absorbent article in the form of a catamenial pad, sanitary napkin 20, is shown in FIG. 7. As used herein, the term "sanitary napkin" refers to an absorbent article which is worn by females adjacent to the pudendal region, generally external to the urogenital region, and which is intended to absorb and contain menstrual fluids and other vaginal discharges from the wearer's body (e.g., blood, menses, and urine). Interlabial devices which reside partially within and partially external of the wearer's vestibule are also within the scope of this invention. As used herein, the term "pudendal" refers to the externally visible female genitalia. It should be understood, however, that the compression resistant web of the present invention is also applicable to other absorbent articles such as panty liners, incontinent briefs, training pants, diapers, and the like. It should be understood, however, that the present invention is not limited to the particular type or configuration of sanitary napkin shown in FIG. 7, but is illustrated herein as a representative, non-limiting example.

The sanitary napkin 20 has two surfaces, a wearer-contacting surface or body-contacting surface, body-facing surface, or "body surface" 20*a* and a garment-facing surface 20*b*. The sanitary napkin 20 is shown in FIG. 7 as viewed from its body surface 20*a*. The body-facing surface 20*a* is intended to be worn adjacent to the body of the wearer. The garment-facing surface 20*b* of the sanitary napkin 20 is on the opposite side and is intended to be placed adjacent to the wearer's undergarments when the sanitary napkin 20 is worn.

The sanitary napkin 20 has two centerlines, a longitudinal centerline "l" and a transverse centerline "t". The term "longitudinal", as used herein, refers to a line, axis or direction in the plane of the sanitary napkin 20 that is generally aligned with (e.g., approximately parallel to) a vertical plane which bisects a standing wearer into left and right body halves when the sanitary napkin 20 is worn. The terms "transverse" or "lateral" as used herein, are interchangeable, and refer to a line, axis or direction which lies within the plane of the sanitary napkin 20 that is generally perpendicular to the longitudinal direction.

FIG. 7 is a top plan view of the sanitary napkin 20 of the present invention in its flat-out state with portions of the structure being cut-away to more clearly show the construction of the sanitary napkin 20 and with the portion which faces or contracts the wearer 20a, oriented towards the viewer. As shown in FIG. 7, the sanitary napkin 20 preferably comprises a liquid pervious compression resistant topsheet 22, a liquid impervious backsheet 23 joined with the compression resistant topsheet 22, and an absorbent core 24 positioned between the compression resistant topsheet 22 and the backsheet 23.

FIG. 7 also shows that the sanitary napkin 20 has a periphery 30 which is defined by the outer edges of the sanitary napkin 20 in which the longitudinal edges (or "side edges") are designated 31 and the end edges or "ends") are designated 32.

Sanitary napkin 20 preferably includes optional side flaps or "wings" 34 that are folded around the crotch portion of the wearer's panties. The side flaps 34 can serve a number f purposes, including, but not limited to protecting the wearer's panties from soiling and keeping the sanitary napkin secured to the wearer's panties.

Figure 8:
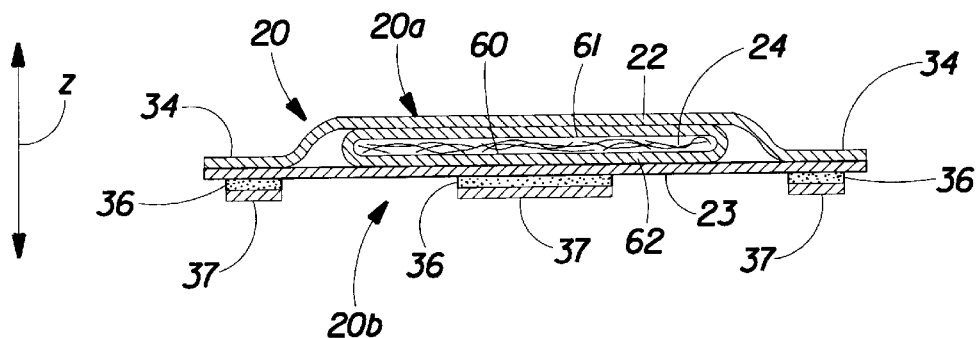
FIG. 8 is a cross-sectional view of the sanitary napkin of FIG. 7 taken along line 8—8.

FIG. 8 is a cross-sectional view of the sanitary napkin 20 taken along section line 8—8 of FIG. 7. As can be seen in FIG. 8, the sanitary napkin 20 preferably includes an adhesive fastening means 36 for attaching the sanitary napkin 20 to the undergarment of the wearer. Removable release liners 37 cover the adhesive fastening means 36 to keep the adhesive from sticking to a surface other than the crotch portion of the undergarment prior to use.

In addition to having a longitudinal direction and a transverse direction, the sanitary napkin 20 also has a "z" direction or axis, which is the direction proceeding down through the compression resistant topsheet 22 and into whatever fluid storage core 24 that may be provided. The objective is to provide a continuous path between the topsheet 22 and underlying layer or layers of the articles herein, such that fluid is eventually drawn in the "z" direction and away from the topsheet of the article into its ultimate storage layer. In a preferred embodiment the continuous path will have a gradient of increasing capillary attraction which facilitates fluid flow down into the storage medium.

In addition to the compression resistant topsheet disclosed herein, specific disclosure of other individual components of the sanitary napkin, such as absorbent core materials, backsheets, and optional features, are disclosed in commonly assigned U.S. Pat. No. 5,342,334 issued Aug. 30, 1994 to Thompson et al., hereby incorporated herein by reference.

Method of Making

The multilayer film 120 of the present invention may be processed using conventional procedures for producing multilayer films on conventional coextruded film-making equipment. In general, polymers can be melt processed into films using either cast or blown film extrusion methods both of which are described in *Plastics Extrusion Technology*—2nd Ed., by Allan A. Griff (Van Nostrand Reinhold—1976), which is hereby incorporated herein by reference. Cast film is extruded through a linear slot die. Generally, the flat web is cooled on a large moving polished metal roll. It quickly cools, and peels off the first roll, passes over one or more auxiliary rolls, then through a set of rubber-coated pull or "haul-off" rolls, and finally to a winder.

In blown film extrusion the melt is extruded upward through a thin annular die opening. This process is also referred to as tubular film extrusion. Air is introduced through the center of the die to inflate the tube and causes it to expand. A moving bubble is thus formed which is held at constant size by simultaneous control of internal air pressure, extrusion rate, and haul-off speed. The tube of film is cooled by air blown through one or more chill rings surrounding the tube. The tube is next collapsed by drawing it into a flattened frame through a pair of pull rolls and into a winder.

A coextrusion process requires more than one extruder and either a coextrusion feedblock or a multi-manifold die system or combination of the two to achieve the multilayer film structure. U.S. Pat. Nos. 4,152,387 and 4,197,069, issued May 1, 1979 and Apr. 8, 1980, respectively, both to Cloeren, are hereby incorporated herein by reference, disclose the feedblock and multi-manifold die principle of coextrusion. Multiple extruders are connected to the feedblock which can employ moveable flow dividers to proportionally change the geometry of each individual flow channel in direct relation to the volume of polymer passing through said flow channels. The flow channels are designed such that at their point of confluence, the materials flow together at the same velocities and pressure minimizing interfacial stress and flow instabilities. Once the materials are joined in the feedblock, they flow into a single manifold die as a composite structure. Other examples of feedblock and die systems are disclosed in *Extrusion Dies for Plastics and Rubber*, W. Michaeli, Hanser, N.Y., $2^{nd}$ Ed., 1992, hereby incorporated herein by reference. It may be important in such processes that the melt viscosities, normal stress differences, and melt temperatures of the material do not differ too greatly. Otherwise, layer encapsulation or flow instabilities may result in the die leading to poor control of layer thickness distribution and defects from non-planar interfaces (e.g. fish eye) in the multilayer film.

An alternative to feedblock coextrusion is a multi-manifold or vane die as disclosed in aforementioned U.S. Pat. Nos. 4,152,387, 4,197,069, as well as U.S. Pat. No. 4,533,308, issued Aug. 6, 1985 to Cloeren, hereby incorporated herein by reference. Whereas in the feedblock system melt streams are brought together outside and prior to entering the die body, in a multi-manifold or vane die each melt stream has its own manifold in the die where the polymers spread independently in their respective manifolds. The melt streams are married near the die exit with each melt stream at full die width. Moveable vanes provide adjustability of the exit of each flow channel in direct proportion to the volume of material flowing through it, allowing the melts to flow together at the same velocity, pressure, and desired width.

Since the melt flow properties and melt temperatures of polymers vary widely, use of a vane die has several advantages. The die lends itself toward thermal isolation characteristics wherein polymers of greatly differing melt temperatures, for example up to 175° F. (80° C.), can be processed together.

Each manifold in a vane die can be designed and tailored to a specific polymer. Thus the flow of each polymer is influenced only by the design of its manifold, and not forces imposed by other polymers. This allows materials with greatly differing melt viscosities to be coextruded into multilayer films. In addition, the vane die also provides the ability to tailor the width of individual manifolds, such that an internal layer can be completely surrounded by the outer layer leaving no exposed edges. The aforementioned patents also disclose the combined use of feedblock systems and vane dies to achieve more complex multilayer structures.

The multilayer film of the present invention comprises two or more layers, at least one of the layers being a rigid layer, with at least one of the remaining layers being substantially less rigid than the rigid layer. In a currently preferred embodiment, rigid skin layer 103 is disposed on the body-facing side of the web, with substantially less rigid layer 101 disposed on the garment-facing side of the web, as shown in FIG. 4. Substantially less rigid layer 101 has opposed first and second sides, one side being substantially continuously joined to one side of rigid layer 103 prior to further processing of the web. Although in a currently preferred embodiment one rigid layer is joined to one substantially less rigid layer, it is contemplated that multiple substantially less rigid layers may be utilized, each substantially less rigid layer being joined to one or two rigid layers. Tie layers, if employed, may each comprise from about 2% to about 10% of the total film thickness.

Once formed into a multilayer film 120, for example as shown in FIG. 5, the substantially flat, smooth polymeric material may be directly formed into a formed film of the present invention, or may be cooled and wound onto a supply roll for further processing. In a preferred process, after the multilayer film has been coextruded it is fed directly to a forming structure for microaperturing, macroaperturing (e.g., via macroscopically expanding), drying (if necessary), and cooling, thereby producing a macroscopically-expanded, three-dimensional, apertured compression resistant web of the present invention.

Figure 9:
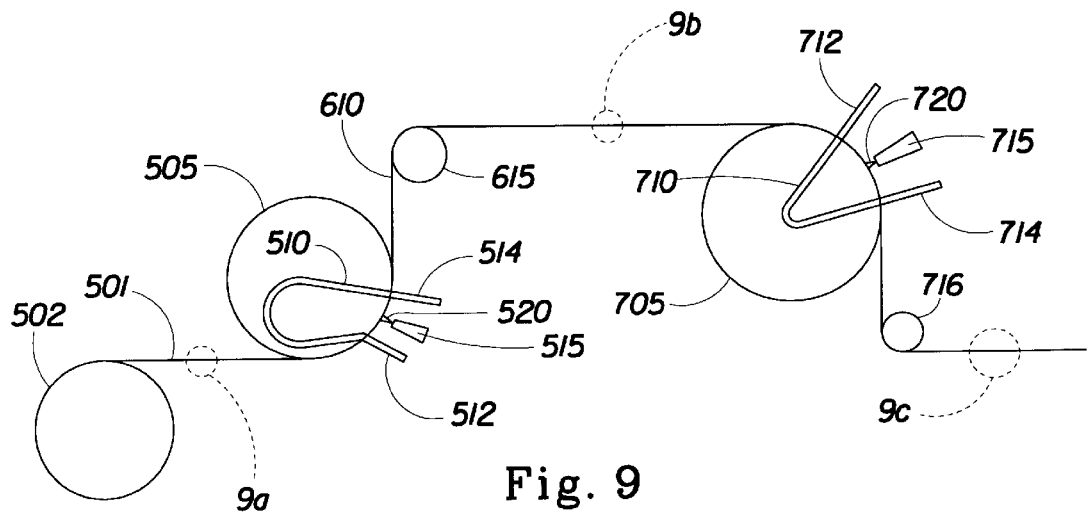
FIG. 9 is a simplified schematic illustration showing an apparatus for forming a web of the present invention.
Figure 9A:
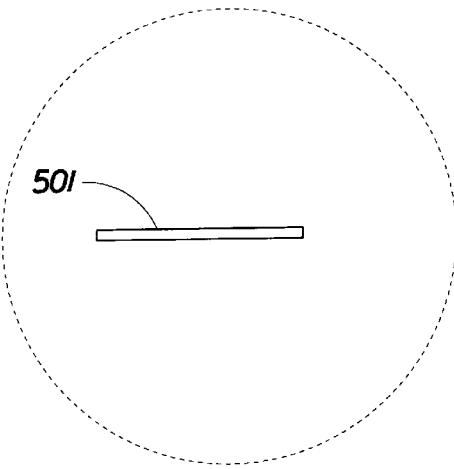
Figure 9B:
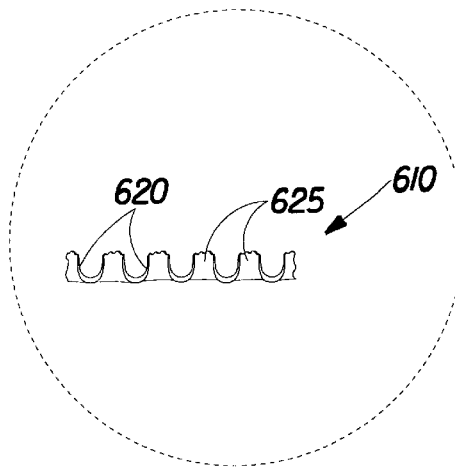

FIG. 9 is a simplified schematic illustration of a particularly preferred process for forming a generally planar polymeric web into a web containing a pattern of microapertured surface aberrations, and further processing the microapertured web to form a macroscopically expanded, apertured three-dimensional web generally similar to that show in FIG. 3. In particular, a web of substantially smooth flat polymeric material 501, corresponding, for example, to film 120 of FIG. 5, is fed from an extrusion process (not shown), or supply roll 502 onto the surface of a woven wire support member 505 which rotates about a stationary vacuum chamber 510. The cross-section of the incoming web 501 is shown in greatly enlarged form in the inset of FIG. 9A. A high pressure liquid jet nozzle 515 is directed at the exposed surface of the substantially smooth flat film 501 intermediate to a pair of baffles 512, 514 as the web traverses the vacuum chamber. The high pressure, i.e., preferably at least about 800 psig, jet of liquid 520 causes the smooth flat web 501 to assume the general contour of the knuckle pattern of the woven wire support member 505. In addition, because the interstices formed by the intersecting filaments are unsupported, the fluid jet causes rupture at those portions of web 501 coinciding with the interstices in the woven wire support structure 505, thereby producing a "planar" microapertured web 610, a segment of which is shown in greatly enlarged form in the inset of FIG. 9B. "Planar" microapertured web 610 exhibits a multiplicity of fine scale surface aberrations 620 generally similar to aberrations 220 of web 80, shown in FIGS. 3 and 4. The microapertures 625 coincide with the point of maximum amplitude of the surface aberrations 620. (It is, of course, recognized that more complex weaving patterns can be utilized to produce more than a single microaperture in any given surface aberration without deviating from the scope of the present invention.)

Planar microapertured web 610 is removed from the surface of woven wire forming structure 505 and passed about idler roll 615. Web 610 is thereafter forwarded with surface aberrations 620 generally outwardly oriented about the periphery of a macroscopic patterned three-dimensional forming structure 705 which rotates about a second stationary vacuum chamber 710. A second high pressure liquid nozzle 715 is located intermediate stationary baffles 712, 714. High pressure liquid nozzle 715 applies a high pressure, i.e., preferably at least about 400 psig, liquid jet 720 substantially across the entire width of planar microapertured web 610. The high pressure liquid jet 720 causes macroscopic expansion of the planar web 610 to a three-dimensional configuration generally resembling that of the forming structure 705 prior to removal about idler roll 716. If, as is preferred, the forming structure exhibits macroscopic cross-section apertures, the high pressure liquid jet will also rupture the end walls of the capillary networks formed in the web.

Figure 9C:
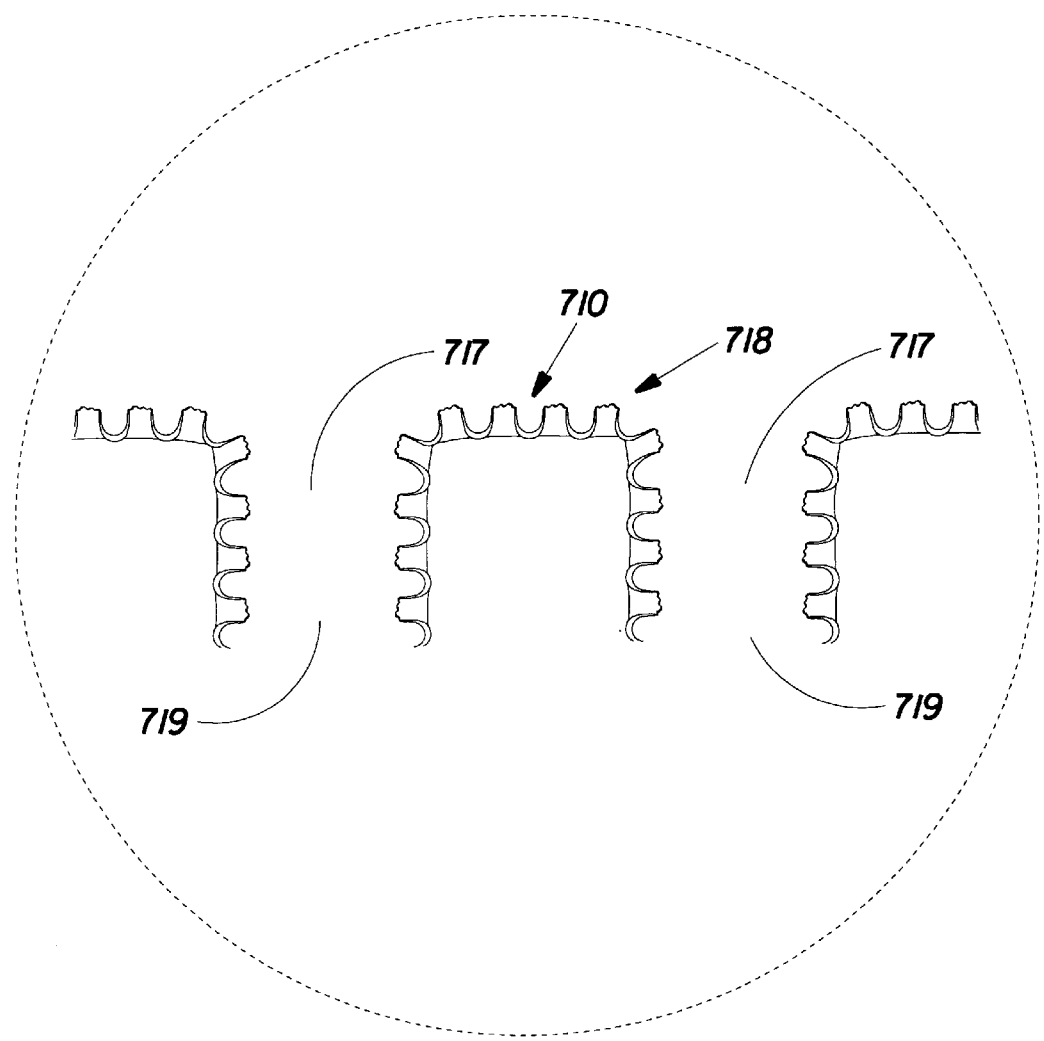

A greatly enlarged segment of the resulting macroscopically expanded and macroscopically apertured web 718 is shown in the inset of FIG. 9C. The macroscopically expanded web 718 exhibits a multiplicity of debossments 717 each having a macroscopic aperture 719 located at its lowermost end. As with the web embodiment 718 illustrated generally in FIG. 9C, the microapertures surface aberrations 610 are outwardly oriented during the macroscopic expansion process so that the skin contacting surface of the macroscopically expanded web 718 comprises the edges of the microapertures 625 formed in each of the surface aberrations.

More specific details as to the nature of the process generally described in relation to FIG. 9 are in the aforementioned Curro '643 patent.

It will be obvious to those skilled in the art that various changes and modifications can be made to the above disclosed invention without departing from the spirit and scope of the present invention. For example, in the event it is desired to produce webs of the present invention wherein a predetermined portion of the web is capable of preventing fluid transmission, it is feasible to perform the processing operation without causing rupture of the web in its second surface. Commonly assigned U.S. Pat. No. 4,395,215 issued to Bishop on Jul. 26, 1983 and commonly assigned U.S. Pat No. 4,747,991 issued to Bishop on May 31, 1988, each of which are hereby incorporated herein by reference, fully disclose how to construct tubular forming structures which are capable of producing three-dimensionally expanded films which are uniformly debossed, but apertured only in predetermined areas.

It is believed that the description contained herein will enable one skilled in the art to practice the present invention in many and varied forms. Nonetheless, the following exemplary embodiment and analytical method is set forth for the purpose of illustrating the beneficial compression resistance of a preferred compression resistant web of the present invention.

EXAMPLES AND COMPARISON TESTING

Exemplary Embodiment

A planar coextruded multilayer film was produced and then formed by methods disclosed above into a compression resistant web of the present invention. The coextruded film comprised two layers as depicted in FIG. 5, with the rigid layer comprising a 30/70 blend of polystyrene/polypropylene and the substantially less rigid layer comprising a blend of LDPE and LLDPE material. Although not required for the compression resistance of the present invention, the polyethylene blend layer comprised titanium oxide as an opacifier, and 1% Atmer 100 as a resin incorporated surfactant. The surfactant causes the finished film (and ultimately the formed film web) to be more wettable, thereby enhancing the fluid flow properties of the web. The total thickness (caliper) of the film was approximately 1.4±0.3 mils with the rigid layer being approximately 10% of the total film thickness prior to forming into a three-dimensional compression resistant web.

Figure 10:
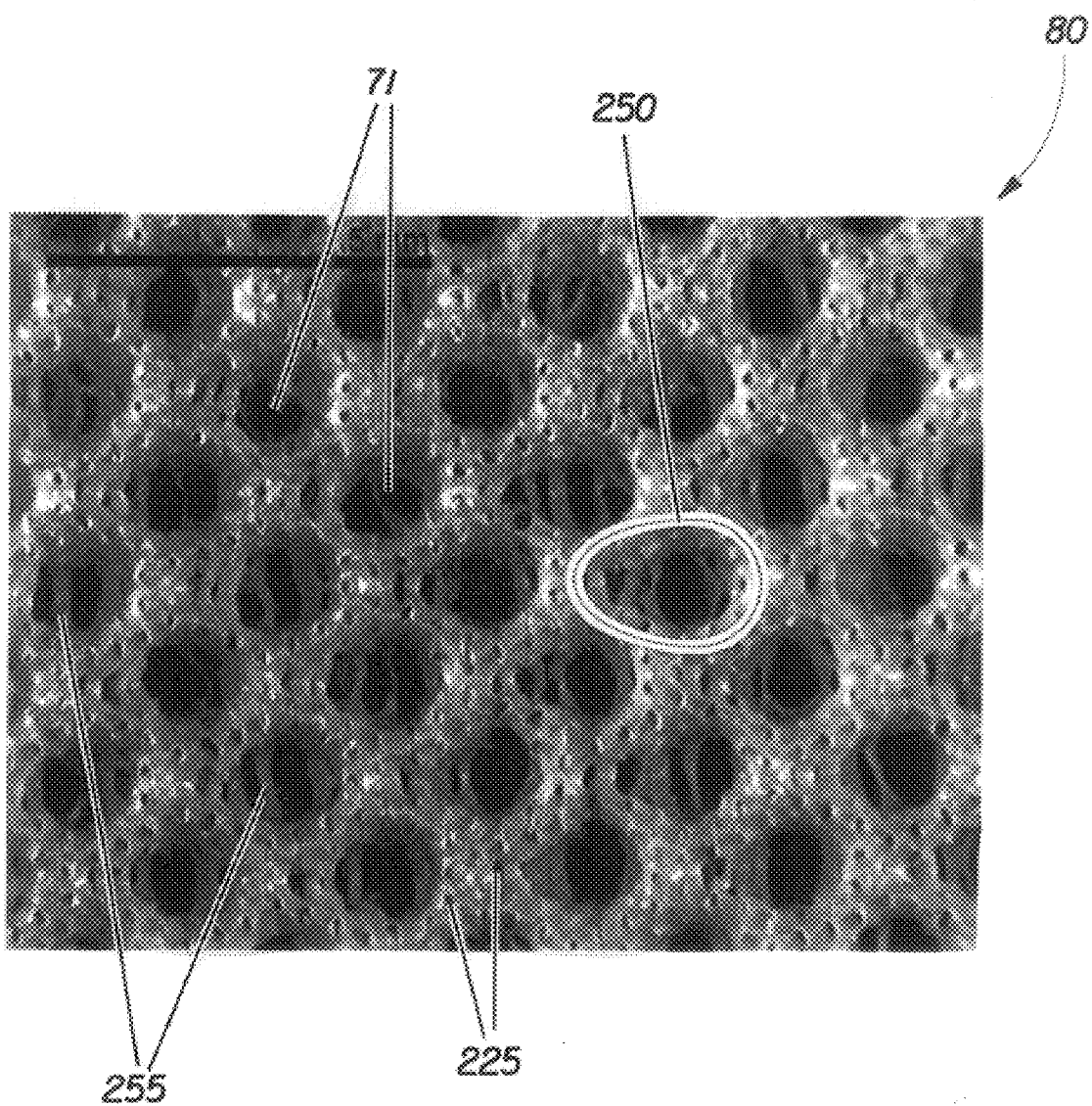
FIG. 10 is a photomicrograph of an Exemplary Embodiment of a web of the present invention.

The coextruded film was processed by the method disclosed above, to form a microapertured, three-dimensional, macroscopically apertured web 80 suitable for use as a compression resistant topsheet (hereinafter, the "topsheet"), as shown in the photomicrograph of FIG. 10. The web 80 comprised a macroaperture 71 density of about 24/cm$^2$, with microapertures 225 formed by a woven wire support member 505 (as shown in FIG. 9) having an 80×80 mesh. While being difficult to measure accurately, the caliper of the topsheet from the first surface to the second surface was approximately 35 mils under about 0.03 psi compression pressure.

As shown in FIG. 10, primary apertures 71 are formed in the general pattern of staggered teardrop shapes, one of which is shown in dotted outline 250. Also shown in FIG. 10 is a plurality of "stringers" 255, which remain as artifacts of the hydroformation process. In general, it is believed that minimizing the number of stringers increases the fluid transport characteristics of the web, while increasing the number of stringers may increase the masking properties of the web. Although, in general, stringers are considered undesirable, the presence or absence of stringers is not believed to impact on the compression resistance of a web of the present invention. However, because stringers are disposed primarily in the plane of the web's second surface, the presence of stringers does provide an additional configuration in which one primary aperture may be characterized as having multiple secondary apertures.

Comparison Testing

A prior art, polyethylene web was produced according to the method disclosed above for comparison purposes in a Caliper versus Compression test. As disclosed above, it has been found that there is a correlation between rewet and retained caliper under compression. The polyethylene web was produced under identical processing parameters as the Exemplary Embodiment, therefore visually appearing similar to the web shown in FIG. 10. However, due to the difference in base film properties, the polyethylene web had a caliper of about 46 mils under about 0.03 psi compression pressure (compared with about 36 mils for the Exemplary Embodiment). As shown below, however, even though starting with a lower relative caliper, the Exemplary Embodiment of a web of the present invention retained a greater caliper under pressure.

Figure 11:
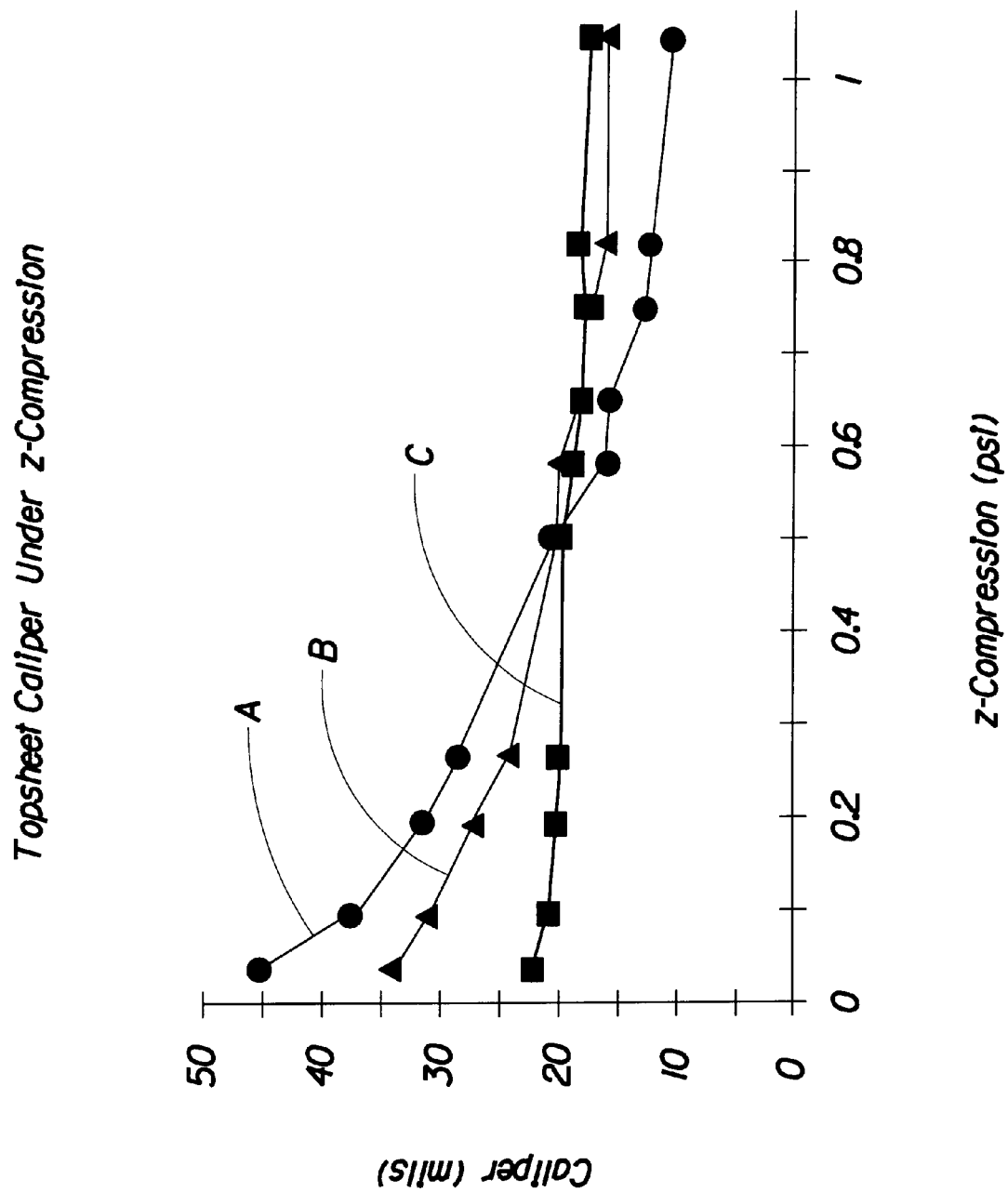
FIG. 11 is a graph illustrating comparison data for compression resistance versus applied pressure for a web of the present invention.

Both the Exemplary Embodiment and the polyethylene web were tested to determine caliper retention with applied pressure, as described below in the ANALYTICAL METHOD section. The data is tabulated in chart form below, and graphically in FIG. 11. The graph of FIG. 11 shows the compression resistance of a polyethylene web graphed as line "A", and the Exemplary Embodiment graphed as line "B". The graph of FIG. 11 also shows the data for a macroscopically expanded web without microapertures, i.e., a prior art, commercially successful web produced according to the teachings of the aforementioned Radel et al., as line "C". It is included graphically as a useful benchmark of desirable compression resistant properties. As noted above, however, such a web without microaperturing lacks the enhanced softness and clothlike texture of microapertured webs, including webs of the present invention.

TABLE 1

Caliper Retention under Compression

| Compression (psi) | AVERAGE CALIPER (mils) | |
|---|---|---|
| | Polyethylene Web | Exemplary Embodiment |
| 0.03 | 46.0 | 36.0 |
| 0.09 | 38.2 | 32.0 |
| 0.19 | 32.2 | 28.0 |
| 0.26 | 29.4 | 25.0 |
| 0.50 | 21.4 | 21.0 |
| 0.58 | 16.8 | 21.0 |
| 0.65 | 16.6 | 19.0 |
| 0.75 | 13.4 | 18.0 |
| 0.82 | 12.8 | 17.0 |
| 1.05 | 11.3 | 17.0 |

As can be seen from Table 1, and graphically in FIG. 11, under pressure, the prior art web comprising only polyethylene (line "A") experienced a caliper change from about 46 mils (at about 0.03 psi) to about 11.3 mils (at about 1.05 psi). This represents a caliper reduction of about 75% under compression pressures of about 1 psi. Caliper reduction is calculated by the following formula:

$$\text{Caliper reduction (\%)} = \frac{(\text{Caliper at about 0.03 psi} - \text{Caliper at about 1.05 psi})}{\text{Caliper at about 0.03 psi}} \times 100$$

Experience has shown that at a caliper of 11.3 mils, the web exhibits significant rewet. The topsheet of the present invention, however, as shown by the compression resistance data of the Exemplary Embodiment (line "B"), experienced a smaller change, from about 36 mils (at about 0.03 psi) to about 17 mils (at about 1.05 psi). This represents a caliper reduction of about 53% under compression pressures of about 1 psi. Furthermore, the retained caliper increases the fluid transport and fluid retaining characteristics of the web. Experience has shown that at a caliper of 17 mils, the web exhibits very little rewet. Therefore, one benefit of the present invention, in addition to softness and clothlike appearance, is the retained caliper under pressure that is beneficial in preventing rewet during use.

ANALYTICAL METHOD

Caliper vs. Compression

An Ames mechanical caliper gauge with a circular pressure foot having 2 in$^2$ area, available from the B.C. Ames Co., of Waltham, Mass., was used to determine the caliper under compression. Appropriate weights were placed atop the piston of the caliper (above gauge) to produce the appropriate pounds per square inch of pressure on the topsheet. The weights used included weights to generate 0.03, 0.09, 0.19, 0.26, 0.50, 0.58, 0.65, 0.75, 0.82, and 1.05 psi pressures. The caliper was "zero-ed" after each time weight atop the piston was changed.

A 7"×12" topsheet to be tested was placed on the marble platform and the caliper foot, with appropriate weights, was gently lowered onto topsheet. After about 10 seconds, the caliper gauge was read to the nearest thousandth of an inch.

A measurement was taken in 5 different areas of the same topsheet. Two sheets of each sample were alternated between weight changes to allow the topsheet to fully recover its embossed thickness before being placed under compression again. The readings for each sample were averaged, and the data are presented in Table 1 above.

What is claimed is:

1. An apertured compression-resistant web comprising a first surface having a plurality of microapertures forming volcano-shaped surface aberrations, a second surface generally parallel to and spaced apart from said first surface, a plurality of fluid passageways extending between said first surface and said second surface to place said first surface and said second surface in fluid communication with one another, said web being formed of a multilayer polymeric film comprising at least one rigid layer and at least one substantially less rigid layer joined to said rigid layer wherein said rigid layer has an elastic modulus of at least 120 kpsi and wherein said substantially less rigid layer has an elastic modulus of not greater than 75 kpsi.

2. An apertured web of claim 1, wherein said rigid layer comprises a material chosen from the group consisting of: polystyrene, high density polyethylene, nylon, polycarbonate, poly(methyl methacrylate), poly(ethylene terephthalate), poly(ethylene 1,4-cyclohexylenedimethylene terepthalate), poly(acrylonitrile-butadiene-styrene), poly(styrene-acrylonitrile), poly(propylene-styrene), poly(propylene-methyl methacrylate) and blends thereof.

3. An apertured web of claim 1, wherein said substantially less rigid layer comprises a material chosen from the group consisting of: low density polyethylene, linear low density polyethylene, ethylene vinyl acetate, metallocene polyethylene, ethylene acrylate copolymers, and ethylene propylene copolymers, styrenic copolymers, ethylene propylene diene polymers, and blends thereof.

4. An apertured web of claim 1, wherein said multilayer film is formed by coextrusion.

5. The multilayer web of claim 1, wherein said multilayer polymeric film has a thickness, and said rigid layer comprises from about 5% to about 40% of said thickness of said multilayer polymeric film.

6. The multilayer web of claim 1, wherein said multilayer polymeric film has a thickness, and said rigid layer comprises less than about 10% of said thickness of said multilayer polymeric film.

7. An apertured compression-resistant web comprising a first surface having a plurality of microapertures forming volcano-shaped surface aberrations, a second surface generally parallel to and spaced apart from said first surface to define a caliper, a plurality of fluid passageways extending between said first surface and said second surface to place said first surface and said second surface in fluid communication with one another, said web experiencing a caliper reduction of less than about 60% under compression pressures of about 1 psi, said web being formed of a multilayer polymeric film comprising at least on rigid layer and at least one substantially less rigid layer joined to said rigid layer wherein said rigid layer has an elastic modulus of at least 120 kpsi and wherein said substantially less rigid layer has an elastic modulus of not greater than 75 kpsi.

8. An apertured web of claim 7, wherein said rigid layer comprises a material chosen from the group consisting of: polystyrene, high density polyethylene, nylon, polycarbonate, poly(methyl methacrylate), poly(ethylene terephthalate), poly(ethylene 1,4-cyclohexylenedimethylene terepthalate), poly(acrylonitrile-butadiene-styrene), poly(styrene-acrylonitrile), poly(propylene-styrene), poly(propylene-methyl methacrylate) and blends thereof.

9. An apertured web of claim 7, wherein said substantially less rigid layer comprises a material chosen from the group consisting of: low density polyethylene, linear low density polyethylene, ethylene vinyl acetate, metallocene polyethylene, ethylene acrylate copolymers, and ethylene propylene copolymers, styrenic copolymers, ethylene propylene diene polymers, and blends thereof.

10. A microapertured, macroscopically-expanded, three-dimensional web having a first surface and a second surface remote from said first surface, said web comprising:
(a) a multilayer formed film comprising at least one rigid layer having an elastic modulus of at least 120 kpsi and at least one substantially less rigid layer having an elastic modulus of not greater than 75 kpsi substantially continuously joined to one side of said rigid layer; and
(b) compression resistant interconnecting members originating substantially concurrently in said first surface as a continuous network defining a plurality of primary apertures, said interconnecting members terminating substantially concurrently in said second surface as a plurality of secondary apertures, each of said primary apertures being in fluid communication with at least one secondary aperture.

11. An apertured web of claim 10, wherein said rigid layer comprises a material chosen from the group consisting of polystyrene, high density polyethylene, nylon, polycarbonate, poly(methyl methacrylate), poly(ethylene terephthalate), poly(ethylene 1,4-cyclohexylenedimethylene terepthalate), poly(acrylonitrile-butadiene-styrene), poly(styrene-acrylonitrile), poly(propylene-styrene), polypropylene-methyl methacrylate) and blends thereof.

12. An apertured web of claim 10, wherein said substantially less rigid layer comprises a material chosen from the group consisting of: low density polyethylene, linear low density polyethylene, ethylene vinyl acetate, metallocene polyethylene, ethylene acrylate copolymers, and ethylene propylene copolymers, styrenic copolymers, ethylene propylene diene polymers, and blends thereof.

13. A disposable absorbent article, said article comprising a compression resistant topsheet, said topsheet comprising an apertured compression-resistant web comprising a first surface having a plurality of microapertures forming volcano-shaped surface aberrations, a second surface generally parallel to and spaced apart from said first surface, a plurality of fluid passageways extending between said first surface and said second surface to place said first surface and said second surface in fluid communication with one another, said web being formed of a multilayer polymeric film comprising at least on rigid layer and at least one substantially less rigid layer joined to said rigid layer wherein said rigid layer has an elastic modulus of at least 120 kpsi and wherein said substantially less rigid layer has an elastic modulus of not greater than 75 kpsi.

14. A disposable absorbent article of claim 13, wherein said article is catamenial pad.

* * * * *

UNITED STATES PATENT AND TRADEMARK OFFICE
CERTIFICATE OF CORRECTION

PATENT NO. : 6,223,187 B1
DATED : April 24, 2001
INVENTOR(S) : David J. Boothby and Robert C. Daley It is certified that error appears in the above-identified patent and that said Letters Patent is hereby corrected as shown below:

<u>Title page,</u>
Item [56], References Cited, OTHER PUBLICATIONS, the first "Chapura, Inc." reference, "http://www.champura.com/3compare.html" should be
-- http://www.chapura.com/3compare/html --.
U.S. Patent No. 5,251,151, "Demjaneko et al." should be -- Demjanenko et al. --.
U.S. Patent No. 5,745,712, "Tuprin et al." should be -- Turpin et al. --.

<u>Column 2,</u>
Line 3, "St. Jose" should be -- San Jose --.

<u>Column 3,</u>
Line 8, after "transmitted", delete the period.
Line 19, after "decreased", insert a period.
Line 23, after "in", delete "a".

<u>Column 4,</u>
Line 23, "computer" should be -- computers --.

<u>Column 6,</u>
Line 9, after "records", delete the period.
Line 55, "'Apr. 1, 1997'" should be -- "April 1, 97" --.
Line 57, "Apr. 1, 1997" should be -- "4-1-97". --.
Line 63, "St. Jose" should be -- San Jose --.

<u>Column 7,</u>
Line 50, after "records", delete the period.

<u>Column 9,</u>
Line 26, "examine" should be -- examines --.

<u>Column 10,</u>
Line 23, "use" should be -- used --.

<u>Column 11,</u>
Line 59, "IDS" should be -- IDs --.

UNITED STATES PATENT AND TRADEMARK OFFICE
CERTIFICATE OF CORRECTION

PATENT NO.   : 6,223,187 B1
DATED        : April 24, 2001
INVENTOR(S)  : David J. Boothby and Robert C. Daley It is certified that error appears in the above-identified patent and that said Letters Patent is hereby corrected as shown below:

<u>Column 12,</u>
Line 1, "database" should be -- databases --.
Line 48, "contains" should be -- contain --.

<u>Column 15,</u>
Line 20, "can not" should be -- cannot --.

Signed and Sealed this

Third Day of December, 2002

JAMES E. ROGAN
*Director of the United States Patent and Trademark Office*